United States Patent [19]

Herkes et al.

[11] Patent Number: 5,898,085
[45] Date of Patent: Apr. 27, 1999

[54] PRODUCTION OF 1,3-DIAMINOPENTANE BY HYDROGENATION OF 3-AMINOPENTANENITRILE

[75] Inventors: Frank Edward Herkes; Jay Leslie Snyder, both of Wilmington, Del.

[73] Assignee: E. I. du Pont de Nemours and Company, Wilmington, Del.

[21] Appl. No.: 09/048,811

[22] Filed: Mar. 26, 1998

Related U.S. Application Data

[60] Provisional application No. 60/042,127, Mar. 28, 1997.

[51] Int. Cl.$^6$ .................................................. C07C 209/02
[52] U.S. Cl. ............................................................ 564/490
[58] Field of Search ..................................... 564/490, 491, 564/493

[56] References Cited

U.S. PATENT DOCUMENTS

| | | | |
|---|---|---|---|
| 4,211,725 | 7/1980 | Kluger et al. | 260/583 P |
| 4,721,811 | 1/1988 | Sherwin et al. | 564/491 |
| 4,885,391 | 12/1989 | Herkes | 564/491 |
| 5,789,621 | 8/1998 | Schnurr et al. | 564/490 |

*Primary Examiner*—Brian M. Burn

[57] ABSTRACT

A process for the hydrogenation of 3-aminopentanenitrile to produce 1,3 diaminopentane using a Raney® cobalt catalyst promoted with chromium, nickel, molybdenum, iron, manganese or mixtures thereof. Performing the reaction in the presence of aqueous caustic (e.g., alkali metal hydroxide) enhances the selectivity to 1,3 diaminopentane.

3 Claims, No Drawings

PRODUCTION OF 1,3-DIAMINOPENTANE BY HYDROGENATION OF 3-AMINOPENTANENITRILE

CROSS-REFERENCE TO RELATED APPLICATIONS

Applicants claim the benefit of priority to provisional application 60/042,127 filed Mar. 28, 1997.

BACKGROUND OF THE INVENTION

1. Field of the Invention

The present invention concerns a process for the preparation of 1,3-diaminopentane by hydrogenation of 3-aminopentanenitrile in the presence of a Raney® cobalt catalyst. More specifically, but not by way of limitation, the present invention relates to the selective production of 1,3 diaminopentane by use of a Raney® cobalt catalyst in the presence of an aqueous caustic solution.

2. Description of Related Art

U.S. Pat. No. 4,211,725 discloses in example 7, the use of Raney® nickel for the reduction of 3-aminopentanenitrile to 1,3-diaminopentane in 76% yield.

U.S. Pat. No. 4,885,391 discloses the use of Raney® cobalt which is promoted with chromium as a catalyst for the hydrogenation of $C_4$ to $C_{12}$ nitrites. In this patent, catalyst activity is maintained by the addition of water.

The known process for hydrogenation of 3-aminopentanenitrile with Raney® nickel has a problem in that it produces by-products 1-methyl and 1-ethyl-3-ethylhexahydropyrimidines and 1,3-diaminopentane dimer high boilers.

SUMMARY OF THE INVENTION

The present invention involves an improved catalytic process for the selective conversion of 3-aminopentanenitrile to 1,3-diaminopentane by reacting 3-aminopentanenitrile with hydrogen in the presence of a catalyst of Raney® cobalt which contains from about 1 to 5% by weight of at least one promoter and optionally up to 5% by weight of an aqueous caustic solution. Surprisingly the use of promoted Raney® cobalt as the catalyst for this reaction avoids production of by-products and produces yields of 1,3-diaminopentane approaching 94.6% or higher.

Thus the present invention provides a process for the conversion of 3-aminopentanenitrile to 1,3-diaminopentane comprising the steps of: (i) contacting a mixture containing 3-aminopentanenitrile with hydrogen in the presence of a catalyst of Raney® cobalt which contains 1 to 5% by weight of at least one promoter chosen from the group consisting of nickel, chromium, molybdenum, iron and manganese at a pressure in the range of 300 to 3,000 psig and at a temperature in the range of 70 to 140° C. for a time sufficient to convert at least a portion of said 3-aminopentanenitrile to 1,3-diaminopentane and (ii) then recovering said 1,3-diaminopentane. Preferably the process is performed at a pressure in the range of 800 to 1,000 psig hydrogen. In one embodiment the process involves contacting of the mixture containing 3-aminopentanenitrile with hydrogen in the presence of a catalyst of Raney® cobalt and further in the presence of up to 5 weight % of an aqueous caustic solution containing from 100 to 5,000 ppm of an alkali metal or alkaline earth metal oxide or hydroxide.

DETAILED DESCRIPTION OF THE INVENTION

The hydrogenation of 3-aminopentanenitrile to 1,3-diaminopentane according to the present invention is catalyzed by Raney® cobalt preferably containing one or more additional metals as promoters. These promoters include nickel, chromium, molybdenum, iron and manganese. Such catalysts and methods for preparing them are described in U.S. Pat. No. 4,721,811 and are commercially available from W. R. Grace.

The hydrogenation reaction according to the instant invention can be performed at a pressure of from about 300 to about 3,000 psig. The upper limit is due to the practical economic considerations of running high pressure reactions rather than due to the chemistry itself. The preferred pressure range is from 800 to 1,000 psig. The reaction may be performed at a temperature of from about 70 to about 140° C. and is preferably carried out at between 80 and 100° C.

The improved process according to the present invention may be performed either in the absence of water addition or in the presence of up to about 5 weight percent, relative to 3-aminopentanenitrile, of an aqueous caustic solution. The aqueous caustic solution is typically present in an amount of about 1 to 5% by weight. The caustic is typically any strong alkali or alkaline earth metal oxide, hydroxide, or equivalent. Typically sodium hydroxide is used as the caustic. The amount of caustic may be in the range of about 100 ppm to about 5,000 ppm.

No additional solvent is needed for the present reaction. However, additional solvent may be used as long as it does not interfere with the reaction. Suitable solvents are described in U.S. Pat. No. 4,721,811.

When the process of the present invention is carried out using a fixed bed catalyst, the catalyst may be placed in an elongated vertical reactor, and the 3-aminopentanenitrile, hydrogen, and the optional base and water fed to the upper end of the reactor. The 1,3-diaminopentane product can be removed through the lower end of the reactor. The 1,3-diaminopentane can be separated from other components by conventional separation means including distillation. In a large scale continuous system, it may be desirable to have present in the reactor a fluid that will serve as a heat sink since the reaction is exothermic. A suitable fluid is a portion of the reaction product that has been cooled and is recycled. By using the cooled, recycled reaction product as the heat sink, it is unnecessary to carry out separation steps for the heat sink fluid; however, if desired other fluids could be used. Examples of other fluids are solvents for the nitrile as set out in U.S. Pat. No. 4,721,811.

When the process of the invention is carried out using a slurry of catalyst, the finely divided catalyst is stirred while in contact with the mixture containing 3-aminopentanenitrile and hydrogen. Optionally, water and base may be present in the reactor.

The following examples are presented to more fully demonstrate and further illustrate various individual aspects and features of the present invention while the comparative example (use of Raney® Ni catalyst) is intended to further illustrate the differences and advantages of the present invention. As such the examples are felt to be non-limiting and are meant to illustrate the invention but are not meant to be unduly limiting in any way.

EXAMPLE 1

Reduction of 3-aminopentanenitrile with Raney® Co catalyst water and caustic

Ninety six grams (0.89 mole, 99%) of 3-aminopentanenitrile, 2 grams of water and 2.0 grams of a 5% NaOH solution were charged to a 300 mL Stainless Steel Autoclave Engineers magnedrive packless autoclave equipped with a thermocouple, cooling coils, sample dip tube containing a stainless steel 5 micron Mott filter and Dispersimix turbine type draft tube agitator containing a rotating impeller. Raney® Co (2.0 g on a dry basis, Raney® 2724 supplied by W. R Grace) catalyst was next charged to the reactor. After closing, the reactor was purged 3 times with hydrogen. The temperature was raised to 90° C. under 50 psig hydrogen with very slow stirring. At reaction temperature, the pressure was raised to 800 psig with hydrogen and maximum (about 1200 rpm's) stirring commenced. Under these conditions, reduction to the desired 1,3-diaminopentane required approximately 120 minutes. Hydrogen uptake kinetics were followed by the pressure drop in a 1 liter hydrogen reservoir feeding the autoclave and transmitted to a Yokogawa HR1300 recorder. Hydrogen uptake data collected every minute throughout the run were monitored both graphically and electronically, and fed into a data file for analysis.

GC analysis of the product was performed on a Hewlett Packard 5890 gas chromatograph GC, equipped with a DB1701 (5% crosslinked phenyl-methylsilicone) megabore column (30 m long, 0.33 ID, 0.25 micrometer film thickness) and a flame ionization detector employing an internal standard of decane. The temperature program was 60° C. for 2 minutes followed by raising at the rate of 8° C./min to 230° C. followed by a 15 minute hold. The column flow rate was 1.5 cc/min helium and split vent flow rate of 60 cc/min helium. The injector and detector temperatures were 250° C. and 265° C., respectively. Analysis of the filtered product on a water free basis showed a 99.5% yield of 1,3-diaminopentane.

EXAMPLE 2

Reduction of 3-Aminopentanenitrile with Raney® Co catalyst and caustic addition

3-Aminopentanenitrile (5.0 grams) and 0.05 grams of 5% NaOH was charged to a 20 ml cylindrical glass bottle containing 0.10 grams Raney® Co (dry basis, Raney® 2724). The glass tube was inserted into a jacketed stainless steel tube, containing a port for gas addition and sealed. The tube was heated and shaken at 100° C. for 2 hours under 800 psig hydrogen pressure. Upon completion, the tube was cooled, depressured and product filtered from the catalyst. Analysis of the liquid product was performed on a 30 m×0.5 mm DB1701 megabore capillary column. GC analysis indicated complete conversion of the 3-aminopentanenitrile to 96.9% yield of 1,3-diaminopentane.

COMPARATIVE EXAMPLE

Reduction of 3-Aminopentanenitrile with Raney® Ni catalyst and caustic addition

3-Aminopentanenitrile (5.0 grams) and 0.05 grams of 5% NaOH was charged to a 20 ml cylindrical glass bottle containing 0.10 grams Raney® Ni (dry basis, Raney® 2400). The glass tube was inserted into a jacketed stainless steel tube, containing a port for gas addition and sealed. The tube was heated and shaken at 100° C. for 2 hours under 800 psig hydrogen pressure. Upon completion, the tube was cooled, depressured and product filtered from the catalyst. Analysis of the liquid product was performed on a 30 m×0.5 mm DB1701 megabore capillary column. GC analysis indicated complete conversion of the 3-aminopentanenitrile to 86.9% yield of 1,3-diaminopentane and 1.3% hexahydropyrimidine by-products. The GC analysis also indicated the presence of unstable intermediates as evidenced by several broad misshapen peaks. A number of high boilers were also produced in 9.2% yield.

EXAMPLE 3

Reduction of 3-Aminopentanenitrile with Raney® Co catalyst without water or base Ninety six grams (0.88 mole, 99%) of 3-aminopentanenitrile was charged to a 300 mL Stainless Steel Autoclave Engineers magnedrive packless autoclave equipped with a thermocouple, cooling coils, sample dip tube containing a stainless steel 5 micron Mott filter and Dispersimix turbine type draft tube agitator containing a rotating impeller. Raney® Co (2.0 grams on a dry basis, Raney® 2724) catalyst was next charged to the reactor. After closing, the reactor was purged 3 times with hydrogen. The temperature was raised to 90° C. under 50 psig hydrogen with very slow stirring. At reaction temperature, the pressure was raised to 800 psig with hydrogen and maximum (about 1200 rpm's) stirring commenced. Under these conditions, reduction to the desired 1,3-diaminopentane required approximately 120 minutes. GC analysis of the filtered product on a water free basis showed a 94.6% yield of 1,3-diaminopentane and 0.9% yield of hexahydropyridines.

Having thus described and exemplified the invention with a certain degree of particularity, it should be appreciated that the following claims are not to be so limited but are to be afforded a scope commensurate with the wording of each element of the claim and equivalents thereof.

We claim:

1. A process for the conversion of 3-aminopentanenitrile to 1,3-diaminopentane comprising the steps of: (i) contacting a mixture containing 3-aminopentanenitrile with hydrogen in the presence of a catalyst of Raney® cobalt which contains 1 to 5% by weight of at least one promoter chosen from the group consisting of nickel, chromium, molybdenum, iron and manganese at a pressure in the range of 300 to 3,000 psig and at a temperature in the range of 70 to 140° C. for a time sufficient to convert at least a portion of said 3-aminopentanenitrile to 1,3-diaminopentane and (ii) then recovering said 1,3-diaminopentane.

2. The process of claim 1 wherein the pressure is in the range of 800 to 1,000 psig and the temperature is in the range of 80 and 100° C.

3. The process of claim 1 wherein said contacting of said mixture containing 3-aminopentanenitrile with hydrogen in the presence of a catalyst of Raney® cobalt is further in the presence of up to 5 weight % of an aqueous caustic solution containing from 100 to 5,000 ppm of an alkali metal or alkaline earth metal oxide or hydroxide.

* * * * *